United States Patent [19]

Ferrato et al.

[11] Patent Number: 4,931,209

[45] Date of Patent: Jun. 5, 1990

[54] LIQUID CRYSTALLINE MATERIALS AND METHOD OF MAKING

[75] Inventors: Joseph P. Ferrato; Julie C. Ferrato, both of Akron, Ohio

[73] Assignee: Crystaloid Electronics, Inc., Hudson, Ohio

[21] Appl. No.: 911,318

[22] Filed: Sep. 25, 1986

[51] Int. Cl.$^5$ .................. G02F 1/13; C09K 19/30; C07C 121/60; C07C 121/48; C07C 121/75

[52] U.S. Cl. .................. 252/299.63; 252/299.5; 350/350 R; 350/350 S; 558/419; 558/420; 558/423

[58] Field of Search ............ 558/423, 420, 419; 252/299.63, 299.5; 350/350 S, 350 R

[56] References Cited

U.S. PATENT DOCUMENTS

| | | | |
|---|---|---|---|
| 4,261,651 | 4/1981 | Gray et al. | 252/299.63 |
| 4,357,078 | 11/1982 | Carr et al. | 252/299.63 |
| 4,361,494 | 11/1982 | Osman et al. | 252/299.63 |
| 4,400,293 | 8/1983 | Romer et al. | 252/299.63 |
| 4,406,814 | 9/1983 | Ferrato | 252/299.63 |
| 4,510,069 | 4/1985 | Eidenschink et al. | 252/299.63 |
| 4,600,528 | 7/1986 | Eidenschink et al. | 252/299.62 |
| 4,627,933 | 12/1986 | Eidenschink et al. | 252/299.63 |
| 4,629,581 | 12/1986 | Boller et al. | 252/299.63 |
| 4,659,449 | 4/1987 | Ferrato | 252/299.63 |
| 4,846,998 | 7/1989 | Pohl et al. | 252/299.63 |

FOREIGN PATENT DOCUMENTS

| | | | |
|---|---|---|---|
| 84194 | 7/1983 | European Pat. Off. | 252/299.63 |
| 107668 | 1/1985 | European Pat. Off. | 252/299.63 |
| 3510432 | 9/1986 | Fed. Rep. of Germany | 252/299.63 |
| 3510434 | 9/1986 | Fed. Rep. of Germany | 252/299.63 |
| 3608765 | 9/1986 | Fed. Rep. of Germany | 252/299.62 |
| 56-140944 | 11/1981 | Japan | 252/299.63 |
| 57-54137 | 3/1982 | Japan | 252/299.63 |
| 57-59851 | 4/1982 | Japan | 252/299.63 |
| 57-95933 | 6/1982 | Japan | 252/299.63 |
| 2092169 | 8/1982 | United Kingdom | 252/299.63 |
| 8605486 | 9/1986 | World Int. Prop. O. | 252/299.63 |

OTHER PUBLICATIONS

Osman, M. A., Mol. Cryst. Liq. Cryst., vol. 72 (Letters), pp. 291–295, (1982).

Osman, M. A., Mol. Cryst. Liq. Cryst., vol. 82, (Letters), pp. 47–52, (1982).

*Primary Examiner*—Teddy S. Gron
*Attorney, Agent, or Firm*—Oldham & Oldham Co.

[57] ABSTRACT

A new family of liquid crystalline or potential liquid crystalline compounds is made relatively cheaply generally by reducing an acid chlorine derivative alkyl or alkoxy benzene or its analogues of an alkyl cyclohexanoic acid to an alkanol derivative, converting the alkanol derivative to a halide such as the bromide or chloride and reacting said halide with a cyano phenol, cyanodiphenol and related compound to form a compound having the formula of equation 1.

7 Claims, No Drawings

LIQUID CRYSTALLINE MATERIALS AND METHOD OF MAKING

TECHNICAL FIELD

This invention relates to very economical and relatively simple methods of preparing liquid crystalline materials and to said materials. More particularly, this invention relates to crystalline materials of the formula:

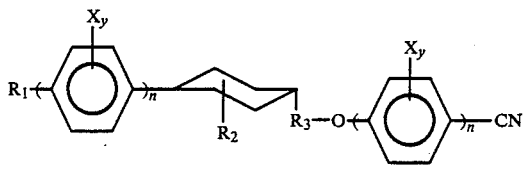

(1)

where $R_1$ is alkyl or alkoxy groups with usually 1 to 8 carbon atoms or alkyl cyclohexyl of 7 or more and preferably 8 to 12 carbon atoms, $R_2$ is an alkyl or alkoxy radical, preferably of 1 to 3 carbon atoms, hydrogen, cyano and halogen and preferably fluorine, $R_3$ is an alkylene, preferably methylene, n is 1, 2, or 3, and $X_y$ is an alkyl or alkoxy, halogen, preferably the fluorine or a nitrile group that has replaced hydrogen in the ring, and y has whole number values of 0 to 4 the y of the $X_y$ radical represents the hydrogens on the ring that has been replaced by $X_y$ radicals, with the understanding $R_1$, $R_2$ and $X_y$ can be selected from the same or different radicals.

BACKGROUND ART

Although liquid crystalline materials are relatively old and well known, the manufacture of these materials are relatively difficult and expensive, usually costing several dollars per pound. This method provides a more economical method of preparing new liquid crystalline compounds.

DISCLOSURE OF INVENTION

Alkoxy and alkyl-1-(4'-cyano phenoxy alkyl)-4-(4'-alkyl phenyl) cyclohexanes and related compounds may be made relatively simply and economically for liquid crystalline materials. These liquid crystalline materials are made by converting for example an alkyl or alkoxy phenyl-alkylcyclohexanoic acid or related acid to its acid chloride, the said chloride is converted to the corresponding alkanol of said acid with a suitable reducing agent, and then converting the corresponding alkanol to a corresponding halide, such as the bromide and then further reacting the corresponding halide with a suitable cyanophenol or related hydroxy polybenzene nitrile to give relatively high yields of the desired alkyl- or alkoxy-1(4'-cyanophenoxyalkyl)-4(alkylphenyl) cyclohexane in the simpler composition.

The starting materials are available or can be made according to the teachings of U.S. Pat. No. 4,406,814. For example (alkylphenyl)-alkylcyclohexanoic acid or (alkoxyphenyl)-alkylcyclohexanoic acid; alkylbiphenyl alkylcyclohexanoic acid or (alkoxyphenyl) alkylcyclohexanoic acid are satisfactory starting materials that can be converted to their corresponding acyl chloride derivatives by reacting with phosphorous pentachloride usully under reflux conditions, as taught in U.S. Pat. No. 4,406,814. Also, the alkyl or alkoxybiphenyl alkyl-cyclohexanoic acids can be used to form the acyl chlorides.

The corresponding acyl chlorides are reduced with lithium aluminum tetrahydride in ethyl ether or related solvent to convert the acid chloride group to an alcohol group as shown by the following representative equation:

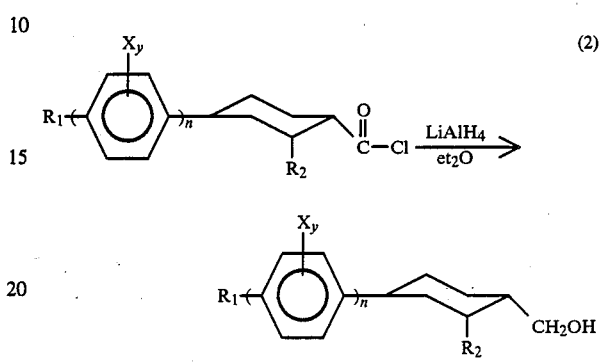

(2)

where n may be 1, 2 or more and preferably 1 or 2, $R_1$ is alkyl or alkoxy preferably of 1 to 8 carbon atoms or alkyl cyclohexyl or alkoxycyclohexyl and $R_2$ is an alkyl or alkoxy group that preferably is methyl or ethyl on at least one of carbons 2 and 3 of the cyclohexane ring and $X_y$ is alkyl or alkoxy, halogen or nitrile and y has values of 0 to 4. The alcohol derivative produced according to the above equation (2), is converted to a halide and preferably a bromide according to the following representative equation:

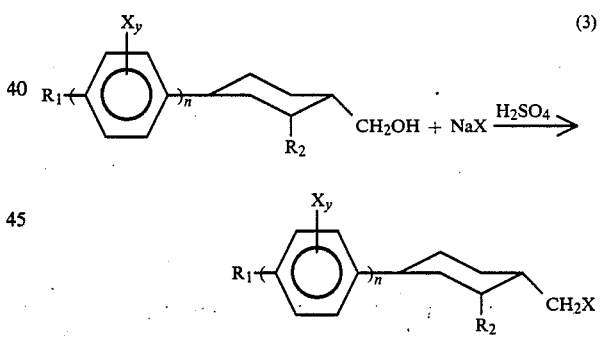

(3)

This halide derivative is then reacted with a suitable cyanophenol according to equation 4 below to give the desired liquid crystalline material:

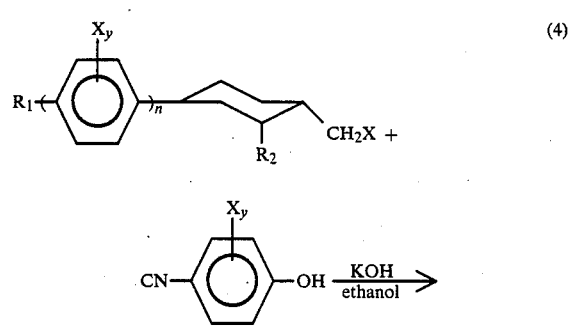

(4)

-continued

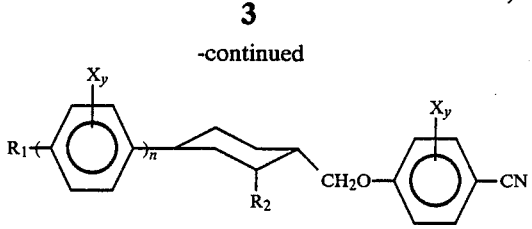

where X is a halide preferably chloride or bromide and $R_1$ and $R_2$ have the values designated for equation 1.

It should be appreciated that the steps of our invention have been illustrated in equations 2, 3 and 4 in the simpler form where n is 1 and the resulting phenylene group has only a single alkyl or alkoxy group thereon. Thus, when the phenylene group contains other substituents such as those described for $X_y$ in formula 1, then the final product of this invention will contain the substituent described in equation 1, such as alkyl, alkoxy, halide or nitrile.

The nature of this invention and its advantages and other aspects may be more readily seen and understood by reference to the following representative and illustrative examples where all parts and percentages are by weight unless otherwise indicated.

EXAMPLE 1

Preparation of the Alkanol Derivative

In a suitable reactor equipped with stirrer cooling means and means to maintain an inert atmosphere and containing 174.3 ml of lithium aluminum tetrahydride, 0.1722 mol of the acid chloride of 2 methyl-4-(4'butoxy phenyl)hexanoic acid in 340 ml of ethyl ether was added dropwise. Care was taken to prevent a violent exothermic reaction between the acyl or acid chloride derivative and the lithium aluminum tetrahydride. After all the acid chloride derivative was added, the mixture was allowed to reflux for two hours and cooled. Any free lithium aluminum tetrahydride in the mixture was neutralized with about 30–60 ml of isopropyl alcohol. The neutralized mixture was mixed with 1.8 ml of water, 77.7 ml of concentrated hydrochloric acid and ice for cooling the mixture. The water phase was separated from the ether phase. The ether phase was washed with four separate aliquots of water and then the washed ether phase was mixed with anhydrous sodium sulfate to remove any water present.

The dry ether phase was filtered and the ether evaporated to leave a crude alkanol derivative in a yield of 92 percent.

Infra red analysis of the solid alkanol derivative showed no carbonyl groups and a strong absorption in the OH group range. This solid product was an alkanol having a melting point of C→I 46.6° C.–50.7° C.

EXAMPLE 2

Preparation of the Halide Derivative From the Alkanol Derivative

The crude alkanol derivative (44 parts) prepared in Example 1 was added to a mixing flask equipped with a magnetic stirrer and a reflux condensor. Then, 40.8 parts of sodium bromide, 51 parts of water and 112.4 ml of 96 percent sulfuric acid was added in the order recited, care being taken to prevent overheating during the addition of the sulfuric acid. The mixture was stirred and refluxed for two hours. The mixture was cooled to room temperature and sufficient hexane was added together with water to break up the emulsion. Then the mixture was extracted three times with hexane. The combined hexane extract was washed three times with 159 ml of 96 percent sulfuric acid. Then the acid-washed hexane extract was neutralized and washed with sodium carbonate. The hexane extract was dried over anhydrous sodium sulfate. The hexane in the dry hexane extract was boiled away to leave the bromide product. This product was passed through a silica gel column using methylene dichloride as the eluent. The eluent was evaporated to leave the chromatographed product in a yield of 52 percent. This product had no alcohol absorption.

EXAMPLE 3

The bromide product, 200 parts, from Example 2 was added to a reactor equipped with a stirrer and reflux condenser that contained 3.96 parts of potassium hydroxide and 7.1 parts of para-cyano phenol dissolved in 86 parts of ethanol. The reaction mixture was allowed to reflux overnight. The reaction mixture was extracted with methylene dichloride. The extract was washed five times with aqueous 7 percent potassium hydroxide and then washed three times with water. The washed extract was dried over anhydrous sodium sulfate. Then the dry extract was passed through a silica gel column using methylene dichloride as the eluent.

The methylene chloride was boiled away from the eluate to leave the reaction product. It was recrystallized in isopropyl alcohol to give a yield of 25 percent with an isotropic/nematic melting point of 87.8°→87.3° C. and N→I 88.3°→88.8° C. and a C→I of 112° C., a unique liquid crystalline product suitable for use in liquid crystalline devices.

The reducing agent may be the reducing lithium aluminum hydrides such as lithium aluminum tetrahydride that is soluble or dispersible in a solvent such as the propyl alcohols and especially isopropyl alcohols and the related alcohols of low boiling point.

The halogenating agent may be an alkali halide such as sodium bromide and a strong mineral acid such as 93 to 99 percent sulfuric acid, a strong acid, preferably a mineral acid, and an alkali halide that yields preferably an insoluble salt to promote the reaction.

The bromide product may be reacted with a cyano phenol or related compounds such as hydroxy biphenyl nitrile by use of suitable alcoholic alkali metal hydroxides. Ethanol solution of potassium hydroxide at reflux conditions is preferred to form the nitrile product.

It should be appreciated the compositions of this invention can be made by the method of this invention by Examples 1 through 3 by using the substituted hexanoic acids listed below as the starting materials:
(methoxy phenyl)-2 $C_1$ to $C_{10}$ cyclohexanoic acid
(methoxy phenyl)-3 $C_1$ to $C_{10}$ cyclohexanoic acid
(butoxy phenyl)-2-ethylcyclohexanoic acid
(decoxy phenyl-1-methylcyclohexanoic acid
(butyl phenyl)-2-fluoro cyclohexanoic acid
(4'-butyl-ethyl phenyl)-2-fluoro cyclohexanoic acid
to name a few of those represented acids which can be formed into the acid chlorides of equation 2.

The phenolic compounds containing nitriles that can be used to form the nitrile of equations are represented as follows:
p-cyanophenol
3,4-dicyanophenol
4(4'-cyanophenyl)-1-hydroxyl benzene
3-fluoro, 4-cyanophenol 2,3,4-tricyanophenol
3,butoxy-4-cyanophenol While in accordance with the patent statutes only the best mode and preferred embodiment of the invention has been illustrated and described in detail, it is to be understood that the invention is not limited thereto or thereby, but that the scope of the invention is defined by the appended claims.

What is claimed is:

1. A compound suitable for use as a liquid crystal having the formula:

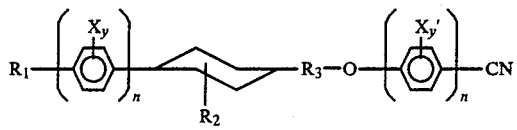

where $R_1$ is alkyl or alkoxy of 1 to 8 carbon atoms, alkylcyclohexyl of 7 to 12 carbon atoms, hydrogen, chloride or cyano, $R_2$ is alkyl alkoxy of 1 to 3 carbon atoms, halide, or cyano and is present at the 2 or 3 position of the transcyclohexyl ring, $R_3$ is methylene, n is 1, 2 or 3, and $X_y$ is an alkyl, alkoxy, halogen or cyano group that has replaced hydrogen in the ring and each of y designates the number of hydrogens that has been replaced on each ring and has values up to 4 and $R_1$, $R_2$, $X_y$ and $X_y'$ can be the same or different radicals.

2. The composition of claim 1 where n is 1 and y' is one.

3. The composition of claim 1 where n is 1 and y' is not 0.

4. The composition of claim 1 where n is 1 and the rings contain an X substituent.

5. The composition of claim 1 where n is 1 $R_1$ is an alkyl of 1 to 8 carbon atoms, and the rings have an X substituent other than alkyl.

6. The composition of claim 1 where n is 1, $R_2$ is alkyl of 1 to 3 carbon atoms and the rings have an X substituent.

7. The composition of claim 1 where the $X_y'$ substituent is fluoride or cyanide.

* * * * *